United States Patent [19]

Wright et al.

[11] Patent Number: 5,125,905

[45] Date of Patent: Jun. 30, 1992

[54] GUIDEWIRE STRAIGHTENER

[75] Inventors: Larry A. Wright, Tampa, Fla.; Peter J. Nicholson, Wilts, England

[73] Assignee: BOC Health Care, Inc., New Providence, N.J.

[21] Appl. No.: 722,725

[22] Filed: Jun. 27, 1991

[51] Int. Cl.$^5$ .............................................. A61M 5/00
[52] U.S. Cl. ...................................... 604/171; 604/93; 604/164; 128/657; 128/772
[58] Field of Search ............... 604/166, 164, 171, 159, 604/172, 158, 163, 280, 283; 128/657, 772

[56] References Cited

U.S. PATENT DOCUMENTS 4,230,110 10/1980 Beroff .............................. 604/280 X
4,235,232 11/1980 Spaven et al. .................. 604/171 X Primary Examiner—John J. Wilson
Assistant Examiner—Jeffrey A. Smith
Attorney, Agent, or Firm—Roger M. Rathbun; Larry R. Cassett

[57] ABSTRACT

A guidewire straightener that is adapted to fit on the end of a protective tube containing a guidewire used for introducing a catheter into a patient's bloodvessel. The guidewire straightener has a flexible end that flexes inwardly to grasp the guidewire when the guidewire is inserted into the end of the protective tube. The guidewire is thus prevented from migrating with respect to the protective tube during packaging, shipping and handling.

3 Claims, 5 Drawing Sheets

GUIDEWIRE STRAIGHTENER

BACKGROUND OF THE INVENTION

This invention relates to a medical guidewire and to a means of protecting such guidewires during shipping and handling.

Guidewires are routinely used in medical procedures where it is desired to introduce a catheter into a patient's blood vessel such as an artery or vein.

In a typical procedure, one approach of utilizing such guidewires for the positioning of a catheter is called the Seldinger technique. In that technique, a catheter introducer is used that has a relatively short flexible cannula that is placed within the patient's blood vessel. Actual insertion of the cannula is assisted by the use of a needle that is positioned within the cannula and is thus inserted in the blood vessel. Upon insertion, the needle is withdrawn, leaving the cannula tip within the blood stream vessel and the body of the catheter introducer external of the patient.

A guidewire is then introduced through the catheter introducer and is extended through the tip of the cannula within the patient's blood vessel until it is positioned with its tip at the desired location within the patient. Upon removal of the catheter introducer, the guidewire remains in the patient and a long catheter is easily slid over the guidewire to the desired position and the guidewire withdrawn. Thus, the catheter remains within the patient having its distal end located at the proper position within the patient's blood vessel.

Such guidewires are delivered through normal shipping channels and are subject to considerable handling prior to and during shipment. The guidewire itself is packaged within a protective tube in a coiled form. Generally, a guidewire straightener fits within the end of the protective tube and the guidewire itself passes through the guidewire straightener and has its end formed into a J configuration just outside the distal end of the guidewire straightener.

The purpose of the guidewire straightener is to provide a channel into which the wire is drawn to straighten out the J configuration just prior to introduction into the patient. Since there normally is no restriction or engagement of the guidewire through the guidewire straightener, the guidewire freely moves with respect to the protective tube and the guidewire straightener.

Unfortunately, the fairly unrestricted movement of the guidewire within its protective tube causes problems in its packaging and later handling. One difficulty arises during packaging since the container within which the guidewire is packaged of necessity is subject to sterilization procedures where a sterilizing material, such as ethylene oxide, is allowed to permeate the plastic package to sterilize the guidewire within that package. The plastic material allows the sterilizing material to pass through to carry out sterilization yet is a barrier to the entry of bacteria.

Accordingly, a problem exists in that the guidewire, once inserted in the package can migrate out of its protective tubing even prior to the sterilization procedure, and can extend outside the normally sealed area, such that when the cover is applied, the guidewire actually extends outside and thus prevents sterilization from becoming effective.

As a further difficulty, during shipment, the guidewire can migrate entirely from its protective tube and remain coiled within its package. As that package is opened by a physician for access to the guidewire, the guidewire is thus unrestrained and can spring out of the package and fall to the floor. Again, obviously, sterilization is breached and the guidewire is unuseable.

Further yet, the wire may migrate from the protective tube during transportation and become kinked within its package. Kinking is irreversable damage to a guidewire and may easily render it unuseable.

SUMMARY OF THE INVENTION

The present invention provides an improved guidewire straightener that includes a flexible proximal end that fits within a protective tube enclosing the guidewire and grips the guidewire to prevent its migration within the protective tube.

The guidewire still passes through the guidewire straightener as in conventional practice, however, the flexible end is sized such that the end flexes inwardly as it is fitted to the end of the protective tubing. As the flexible end moves inwardly, it grasps the guidewire and prevents its movement with respect to the guidewire straightener. Thus, by a relatively simple modification to the guidewire straightener, the problem of guidewire migration experienced during manufacture, transportation and shipping can be prevented, and without any significant extra expense.

The guidewire straightener of the present invention is readily molded as a one piece unit and is useable to alleviate the migration problem without modification to any other component of the guidewire assembly, thus it is easy to facilitate its use in production procedures.

DESCRIPTION OF THE PREFERRED EMBODIMENT

Figure 1:
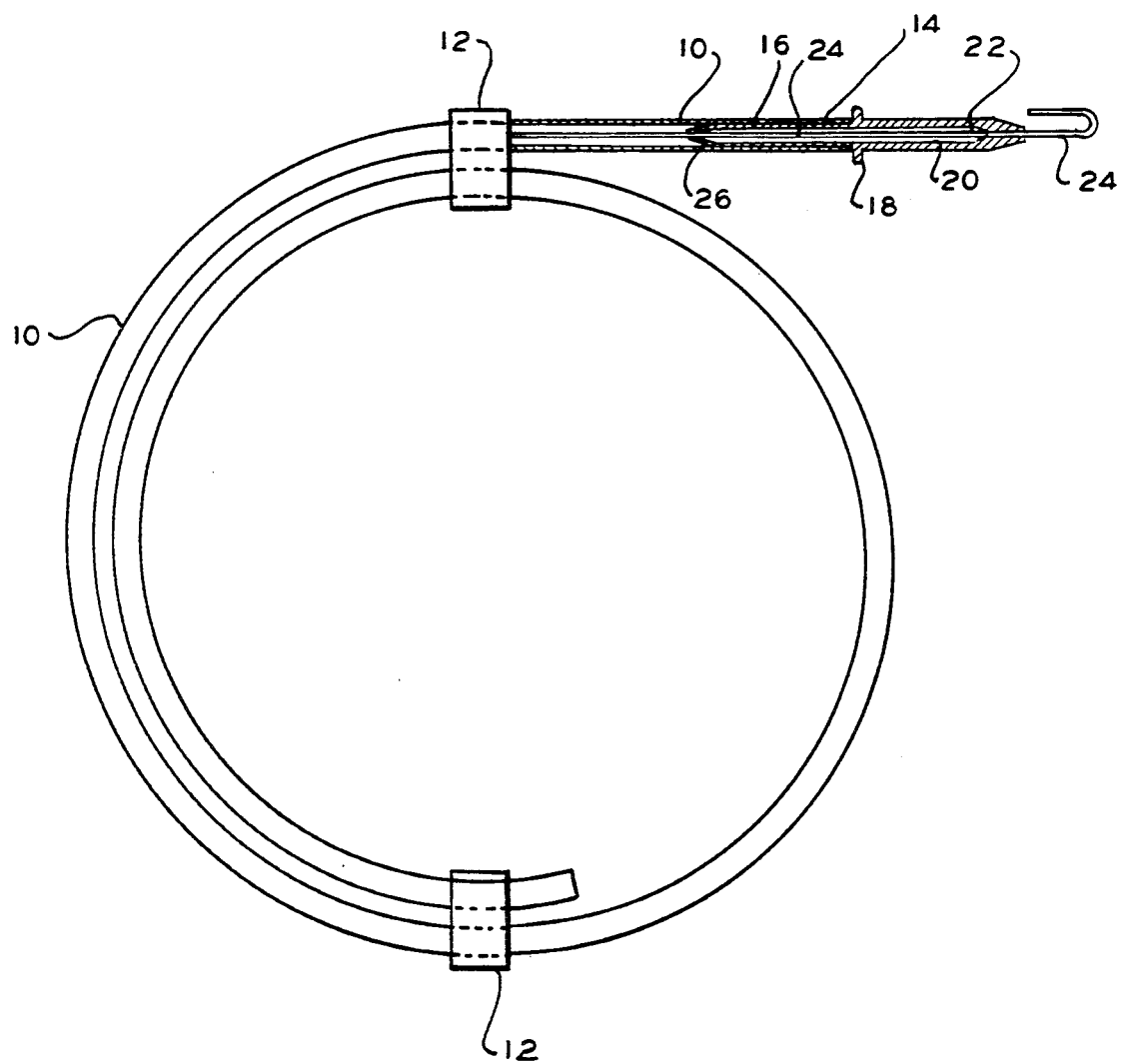
FIG. 1 is a schematic view, partly in section, of a guidewire contained within a protective tube and having a guidewire straightener constructed in accordance with the present invention.
Figure 2A:
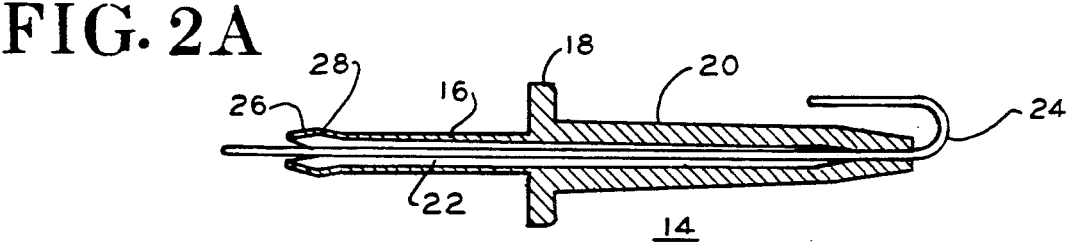
FIG. 2A-2G are a series of cross-sectional views showing a guidewire straightener in which straightening of the guidewire takes place.
Figure 2B:
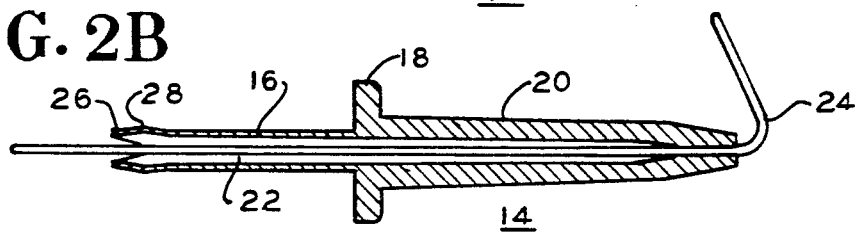
Figure 2C:
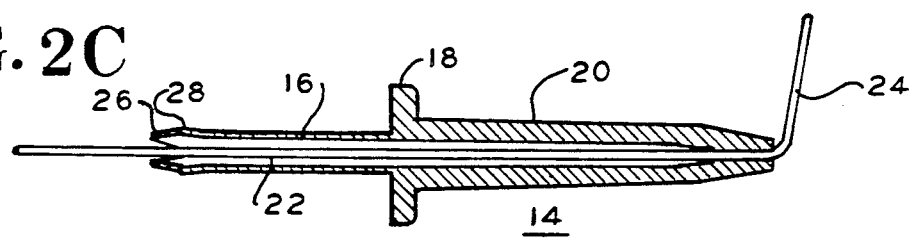
Figure 2D:
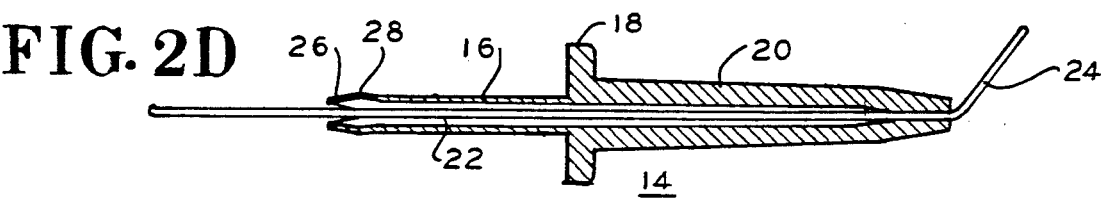
Figure 2E:
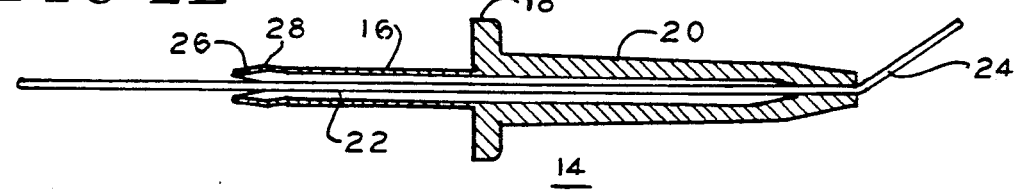
Figure 2F:
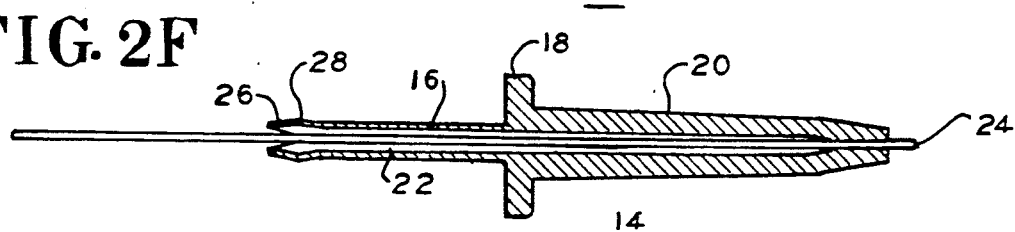
Figure 2G:
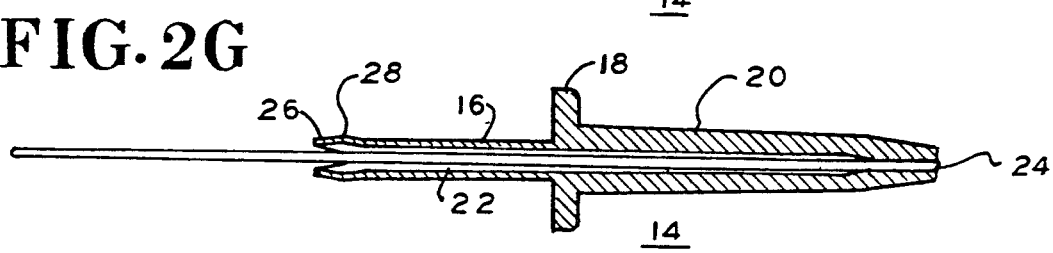

Referring now to FIG. 1, there is shown a plan view, partly in section of a guidewire assembly in the form it is shipped to customers.

A protective plastic tube 10 is coiled within the shipping package and is constrained in the coiled position by means such as a pair of retainers 12. Generally, a sealed package surrounds the plastic tubing and the contents sterilized prior to shipment.

A guidewire straightener 14 is affixed to the distal end of the protective plastic tube 10. In a normal manner, that affixation is by a force fit between the internal diameter of a projecting cylindrical hub 16 formed as part of the guidewire straightener 14. A peripheral flange 18 is also formed as part of the guidewire straightener 14 and, when fitted on to the end of the protective plastic tube 10, the peripheral flange 18 abuts the distal end thereof. The remaining part of the guidewire straightener 14 is a body 20 that is molded to fit within a catheter introducer as will be later explained.

A passageway 22 is formed in the guidewire straightener 14 and through which passes the guidewire 24. As seen in the FIG. 1, the guidewire 24 projects outward from the body 20 and is configured in a J-shape.

At the inner end of cylindrical hub 16, there is formed a flexible end 26 that is designed to flex inwardly as the guidewire straightener 14 is affixed to the distal end of protective plastic tube 10 and which serves to grip the guidewire 24, as will be explained, to prevent its movement within the protective plastic tube 10 during shipping and handling.

Turning now to FIGS. 2A-2G there is shown a series of sequential, cross-sectional views of the guidewire straightener 14 as it is used to straighten the J-shaped end of a guidewire 24 prior to introduction into the blood vessel of a patient.

As can be seen from the sequence of FIGS. 2A-2G, the guidewire 24 is progressively pulled backwardly such that its projecting J-shaped distal end is pulled into the guidewire straightener 14 and the J-shape is removed. As one can also see in FIG. 2A-2G, the flexible end 26 allows the guidewire 24 to readily move with respect to the guidewire straightener 14 since flexible end 26 is no longer compressed by the protective plastic tube 10 (not shown in FIGS. 2A-2G).

When located in the end of the protective plastic tube 10, however, the flexible end 26 has an enlarged diameter ridge 2B that is larger than the inner diameter of protective plastic tube 10 by a predetermined amount. Therefore, in order to force the cylindrical hub 16 into the protective plastic tube 10, the flexible end 26 compresses inwardly and grips the guidewire 24.

Figure 3A:
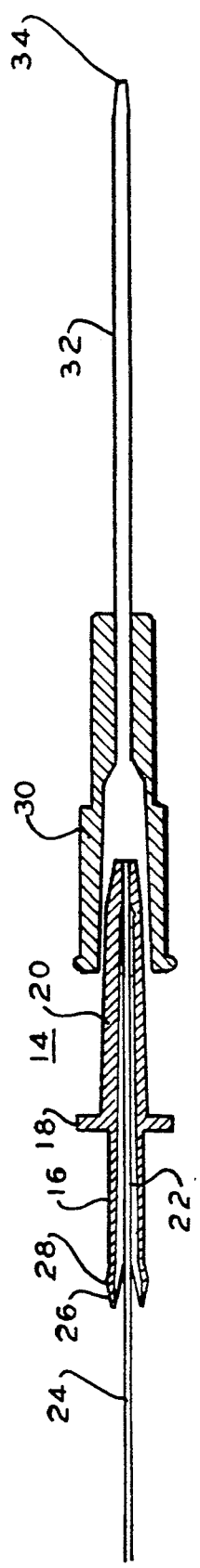
FIG. 3A-3D is a series of cross-sectional views showing the steps of introducing a guidewire through an introducer to the patient's blood vessel.
Figure 3B:
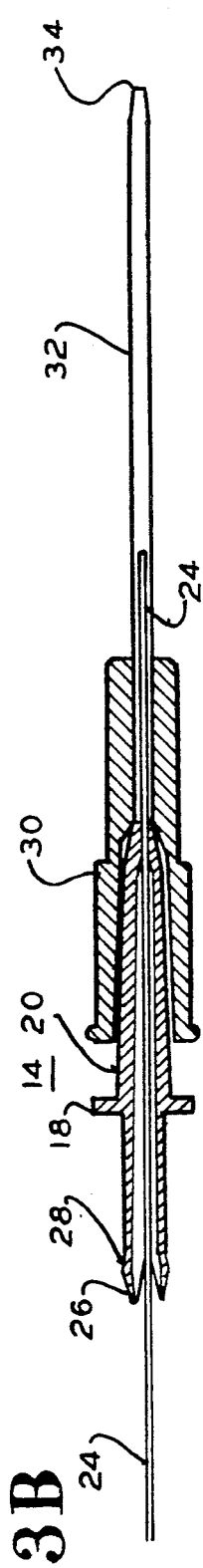
Figure 3C:
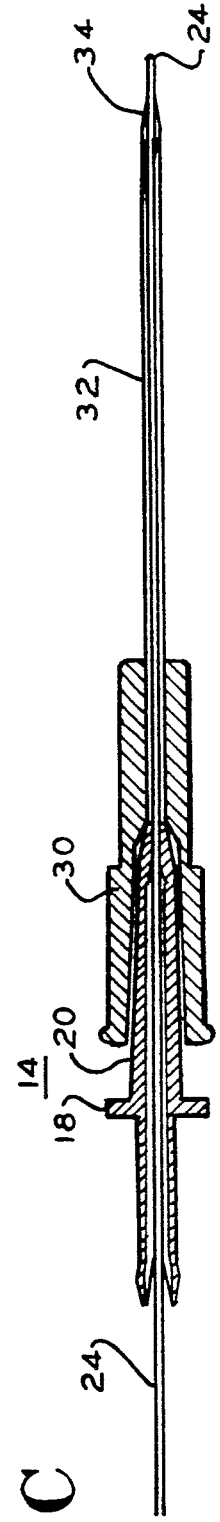
Figure 3D:
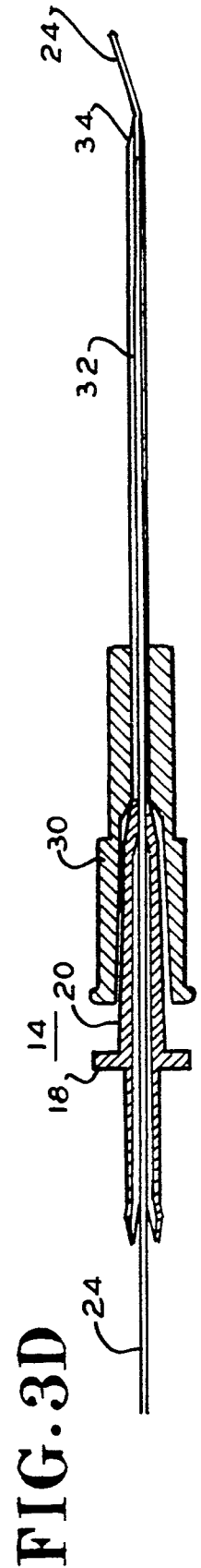

Taking now FIGS. 3A-3D, the advancing of the guidewire 24 into a patient's blood stream can be seen in stepwise progression. In FIG. 3A, the guidewire straightener 14 containing guidewire 24 enters the catheter introducer 30. As noted, catheter introducer 30 has a flexible cannula 32 that is positioned having its distal end 34 in the particular desired blood vessel. As one progresses through the steps, therefore, to FIG. 3B, the guidewire straightener 14 is in position lodged within catheter introducer 30 and the guidewire 24 has progressed into the flexible cannula 32. In FIGS. 3C and 3D therefore, the guidewire 24 reaches the distal end 34 of the flexible cannula 32 and proceeds to enter the patient's blood vessel where it progresses further until it is in the desired position.

Figure 4:
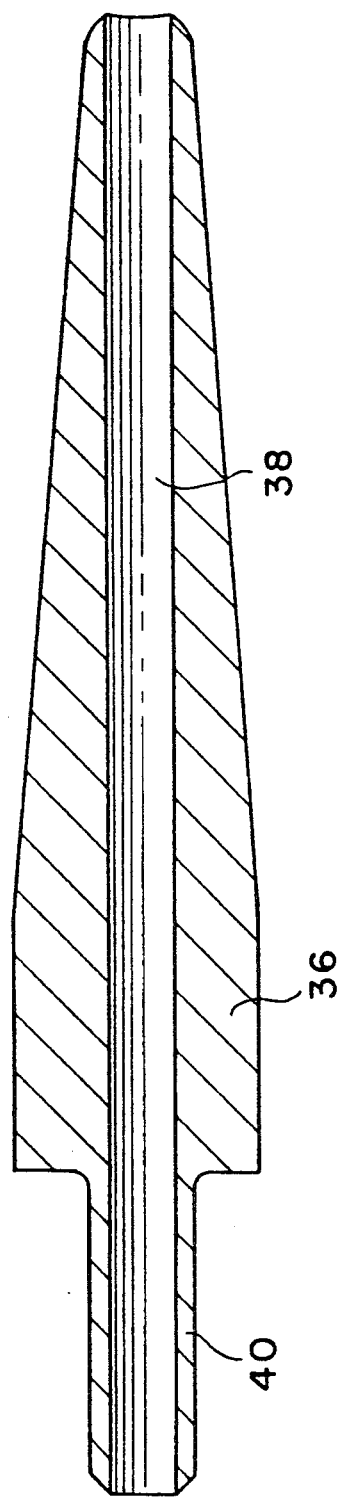
FIG. 4 is a cross-sectional view of a typical prior art guidewire straightener.

In FIG. 4, there is shown a cross-sectional view of a prior art guidewire straightener 36 having a passageway 38 therethrough for containing the guidewire (not shown). A projecting cylindrical hub 40 is formed having a diameter that is manufactured so as to create a force fit when the guidewire straightener 36 is affixed to the end of a protective plastic tube (not shown).

Figure 5:
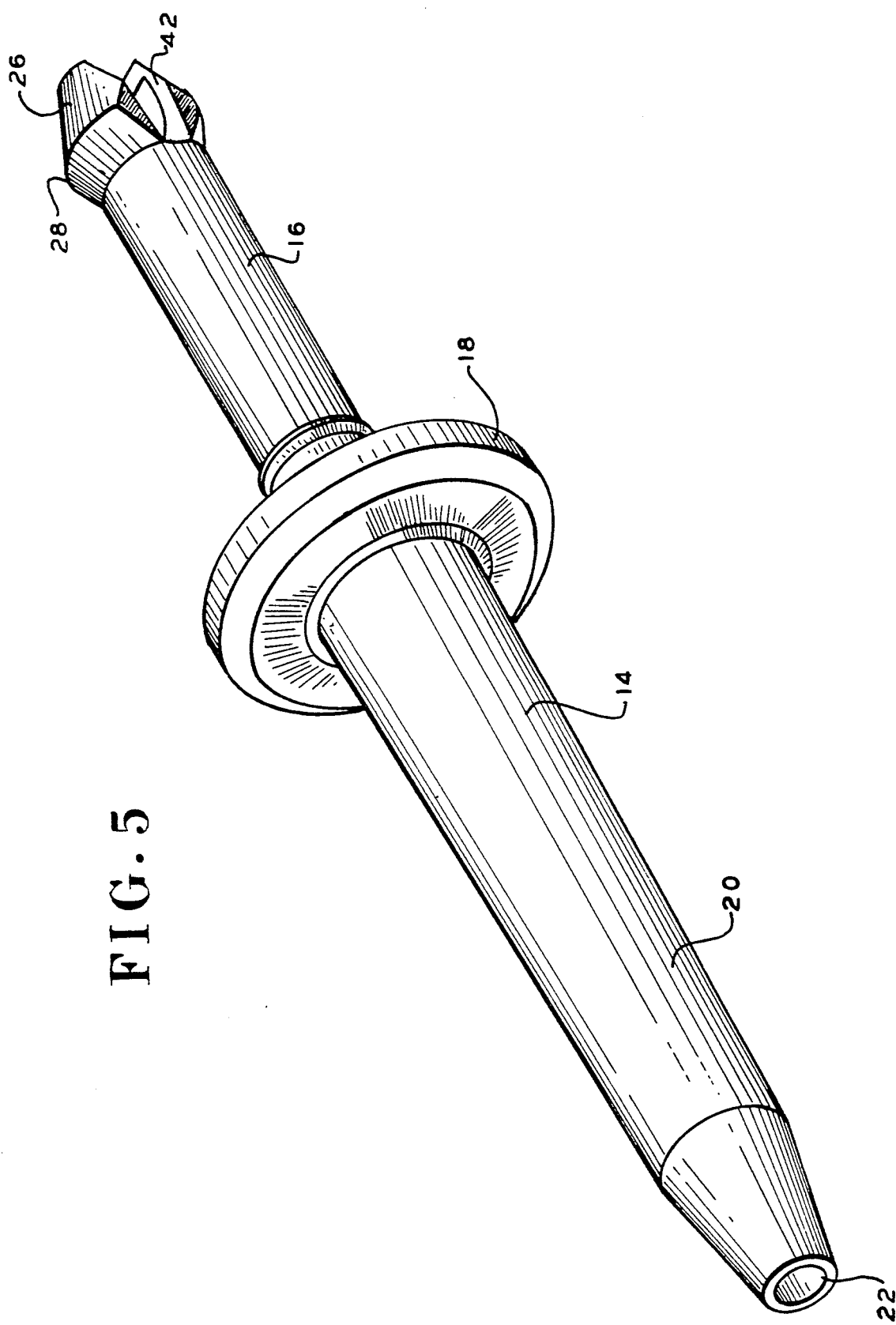
FIG. 5 is an isometric view of a guidewire straightener constructed in accordance with the present invention.

Turning finally to FIG. 5 there is shown an isometric view of the guidewire straightener 14 of the present invention.

The features of the flexible end 26 include a slot 42 formed in flexible end 26 creating a bifurcated end having two tabs. Surrounding the slot 42 is the enlarged diameter ridge 28 of predetermined diameter such that insertion of the guidewire straightener 14 into the protective plastic tubing (FIG. 1) causes the flexible end 26 to pinch inwardly and grip the guidewire 24 (FIG. 1).

Thus the guidewire straightener 14 is a single piece molded of a flexible plastic, such as polypropylene, and which, when assembled to its protective plastic tube, captures the guidewire and thus prevents migration of the guidewire within the protective plastic tubing during packaging, handling and shipping.

We claim:

1. A guidewire straightener adapted to fit on an end of a protective tube having an inner diameter, said guidewire straightener having a through passageway for containing a guidewire and a cylindrical hub having a flexible end having at least one slot and having a predetermined outer diameter to create a force fit when fitted within the inner diameter of the protective tube, said flexible end having a ridge of predetermined greater diameter than said inner diameter of the protective tube and whereby said flexible end constricts inwardly to grasp the guidewire when said cylindrical hub is inserted into the inner diameter of said protective tube.

2. A guidewire straightener as defined in claim 1 wherein said flexible end comprises a plurality of flexible tabs.

3. A method of fixing a guidewire within a protective tube having an inner diameter comprising the steps of:
   a. providing a guidewire straightener having a hub that fits within the inner diameter of the protective tube;
   b. locating a guidewire within the protective tube and extending through the guidewire straightener;
   c. providing a flexible end on the guidewire hub having at least one slot and an enlarged ridge that is larger than the internal diameter of the protective tube; and
   d. placing the guidewire straightener on an end of the protective tube by forcing the hub within the inner diameter of the protective tube to cause the flexible end to constrict inwardly to grasp the guidewire.

* * * * *